US006824990B1

(12) United States Patent
Blumer (10) Patent No.: US 6,824,990 B1
(45) Date of Patent: Nov. 30, 2004

(54) METHODS OF DETECTING AND MODULATING OLIGOMERIZATION OF G PROTEIN-COUPLED RECEPTORS

(75) Inventor: Kendall J. Blumer, St. Louis, MO (US)

(73) Assignee: Washington University, St. Louis, MO (US)

( * ) Notice: Subject to any disclaimer, the term of this patent is extended or adjusted under 35 U.S.C. 154(b) by 16 days.

(21) Appl. No.: 09/679,852

(22) Filed: Oct. 5, 2000

Related U.S. Application Data (60) Provisional application No. 60/157,747, filed on Oct. 5, 1999.

(51) Int. Cl.[7] ...................... G01N 33/53; G01N 33/567; A61K 38/00; C07K 1/00; C07K 14/00
(52) U.S. Cl. ........................ 435/7.1; 435/7.2; 530/300; 530/350; 530/402
(58) Field of Search ........................ 435/7.1, 7.2, 69.1, 435/70.1, 71.1, 71.2, 252.3, 471; 530/300, 350, 402

(56) References Cited

PUBLICATIONS

Gilman AG. et al., The Pharmacological Basis of Therapeutics, 8th ed. McGraw Hill, New York, pp. 33 and 45, 1993.*
Miyawaki A. et al., Nature 388:882–887, 1997.*
Gama L. et al., J. Biol. Chem. 273:29712–29718, 1998.*
Pace et al. "Dimerization of the Calcium–Sensing Receptor Occurs within the Extraceullular Domain and is Eliminated by Cys> Ser Mutations at Cys[101] and Cys[236]" *J Biol Chem* 274(17):11629–11634, Apr. 23, 1999.
Jordan et al. "G–Protein–Coupled Receptor Heterodimerization Modulates Receptor Function" *Nature* 399:697–700, Jun. 1999.
Maggio et al. "G Protein–Linked Receptors: Pharmacological Evidence for the Formation of Heterodimers" *J Pharmacol Exp Ther* 291(1):251–257, 1999.
Kuner et al. "Role of Heteromer Formation in $GABA_B$ Receptor Function" *Science* 283:74–77, Jan. 1999.
Marshall et al. "$GABA_B$ Receptors—The First 7TM Heterodimers" *Trends Pharmacol Sci* 20:396–399, Oct. 1999.
Jones et al. "$GABA_B$ Receptors Function as a Heteromeric Assembly of the Subunits $GABA_BR1$ and $GABA_BR2$" *Nature* 396:674–679, Dec. 17, 1998.
White et al. "Heterodimerization is Required for the Formation of a Functional $GABA_B$ Receptor" *Nature* 396:679–682, Dec. 17, 1998.

Kaupmann et al. "$GABA_B$–Receptor Subtypes Assemble into Functional Heteromeric Complexes" *Nature* 396:683–687, Dec. 17, 1998.
Hebert et al. "Structural and Functional Aspects of G Protein–Coupled Receptor Oligomerization" *Biochem Cell Biol* 76:1–11, 1998.
Stefan et al. "Mechanisms Governing the Activation and Trafficking of Yeast G Protein–Coupled Receptors" *Mol Biol Cell* 9:885–899, Apr. 1998.
Hebert et al. "A Peptide Derived from a $\beta_2$–Adrenergic Receptor Transmembrane Domain Inhibits Both Receptor Dimerization and Activation" *J Biol Chem* 271(27):16384–16392, Jul. 5, 1996.
Ng et al. "Dopamine D2 Receptor Dimers and Receptor–Blocking Peptides" *Biochem Biophys Res Commun* 227:200–204, 1996.
Lemmon et al. "Regulation of Signal Transduction and Signal Diversity by Receptor Oligomerization" *Trends Biochem Sci* 19:459–463, Nov. 1994.
Wade et al. "Multisite Interactions of Receptors and G Proteins: Enhanced Potency of Dimeric Receptor Peptides in Modifying G Protein Function" *Mol Pharmacol* 45:1191–1197, 1994.
Blumer et al. "The STE2 Gene Product is the Ligand–Binding Component of the α–Factor Receptor of *Saccharomyces cerevisiae*" *J Biol Chem* 263(22):10836–10842, Aug. 5, 1988.
Reneke et al. "The Carboxy–Terminal Segment of the Yeast α–Factor Receptor is a Regulatory Domain" *Cell* 55:221–234, Oct. 21, 1988.

* cited by examiner

*Primary Examiner*—Robert Landsman
(74) *Attorney, Agent, or Firm*—Needle & Rosenberg, P.C.

(57) ABSTRACT

The present invention provides a method of detecting oligomerization of G protein coupled receptors comprising: a) obtaining a first G protein coupled receptor fusion protein containing a fluorescence donor; b) obtaining a second C protein coupled receptor fusion protein containing a fluorescence acceptor; c) transfecting a cell with the G protein coupled receptor fusion proteins of a) and b); d) exciting the fluorescence donor at a particular wavelength; e) detecting fluorescence emission of the acceptor (FRET), such that if this emission is greater than the emission detected in control cells expressing only the acceptor, oligomerization of the G protein coupled receptors has been detected. The invention further provides methods of detecting agonists and antagonists of G protein coupled receptors by utilizing FRET.

24 Claims, 6 Drawing Sheets

METHODS OF DETECTING AND MODULATING OLIGOMERIZATION OF G PROTEIN-COUPLED RECEPTORS

This application claims priority to U.S. provisional application Ser. No. 60/157,747 filed on Oct. 5, 1999. The 60/157,747 provisional patent application is herein incorporated by this reference in its entirety.

FIELD OF THE INVENTION

The present invention relates to methods of detecting oligomerization of G protein coupled receptors (GPCRs) as well as to the identification of agonists and antagonists of G protein coupled receptors utilizing fluorescence resonance energy transfer (FRET).

BACKGROUND OF THE INVENTION

Hormones, sensory stimuli, neurotransmitters, chemokines and other molecules signal by activating G protein coupled receptors. These receptors were thought to function as monomers, however, the present invention provides the surprising result that G protein coupled receptors are oligomeric in intact cells and membranes. Therefore, oligomerization of G protein coupled receptors is important for G protein coupled receptor signaling and regulation. By utilizing the methods of the present invention, oligomerization of homologous as well as heterologous G protein coupled receptors can be detected by FRET. Additionally, screening assays are provided for identification of agonists and antagonists of G protein coupled receptors.

SUMMARY OF THE INVENTION

The present invention provides a method of detecting oligomerization of G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) exciting the fluorescence donor at a particular wavelength; e) detecting fluorescence emission of the acceptor (FRET), such that if this emission is greater than the emission detected in control cells expressing only the acceptor, oligomerization of the G protein coupled receptors has been detected.

Also provided by the present invention is a method of determining whether a receptor agonist activates G protein coupled receptors by enhancing oligomerization or activates G protein coupled receptors by disrupting oligomerization comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; e) exciting the fluorescence donor at a particular wavelength; f) detecting fluorescence resonance energy transfer (FRET), such that if the efficiency of FRET detected is greater in the cells contacted with the agonist than the efficiency of FRET detected in cells prior to the addition of the agonist, receptor activation has occurred by enhancing oligomerization and if the efficiency of FRET detected is less in the cells contacted with the agonist than the efficiency of FRET detected in cells prior to the addition of the agonist, receptor activation has occurred by disrupting oligomerization.

The present invention further provides a method of screening for an agonist that activates G protein coupled receptors by enhancing oligomerization comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; e) exciting the fluorescence donor at a particular wavelength; f) detecting fluorescence resonance energy transfer (FRET), such that if the efficiency of FRET detected is greater in the cells contacted with the agonist than the efficiency of FRET detected in cells prior to the addition of the agonist, receptor activation has occurred by enhancing oligomerization.

Further provided by the present invention is a method of screening for an agonist that activates G protein coupled receptors by disrupting oligomerization comprising: a)obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; e) exciting the fluorescence donor at a particular wavelength; f) detecting fluorescence resonance energy transfer (FRET), such that if the efficiency of FRET detected is less in the cells contacted with the agonist than the efficiency of FRET detected in cells prior to the addition of the agonist, receptor activation has occurred by disrupting oligomerization.

The present invention also provides a method of screening for an agonist of the interaction between G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); c) contacting the cell with a test compound; d) exciting the fluorescence donor at a particular wavelength; e) detecting fluorescence resonance energy transfer (FRET), such that if the efficiency of FRET detected is greater in cells contacted with the compound than the efficiency of FRET detected in cells prior to the addition of the test compound, the test compound is an agonist of the interaction between G protein coupled receptors.

The present invention also provides a method of screening for an antagonist of the interaction between G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with a test compound; e) exciting the fluorescence donor at a particular wavelength; e) detecting fluorescence resonance energy transfer FRET), such that if the efficiency of FRET detected is less than the efficiency of FRET detected in cells prior to the addition of the test compound, the test compound is an antagonist of the interaction between G protein coupled receptors.

BRIEF DESCRIPTION OF THE FIGURES

FIGS. 1a–1i shows the use of FRET to detect oligomerization of α-factor receptors in vivo. Yeast cells expressed tailless α-factor receptors fused to CFP or YFP (Ste2-CFP or -YFP) and/or glucose transporters fused to YFP (Hxt1-YFP), as indicated. Untagged α-factor receptors (Ste2) or glucose transporters (Hxt1) were overexpressed where indicated. Intact cells (panels a–g) or plasma membrane fractions (panels h–i) were excited at the $\lambda_{max}$ of CFP (440 nm) and fluorescence emission was detected by scanning fluorometry. Fluorescence emission due to FRET (FRET) was determined as: (emission spectrum of cells co-expressing CFP and YFP fusion proteins)—(emission spectrum of cells expressing CFP fusion alone)—(emission spectrum of cells expressing YFP fusion alone). The efficiency of FRET (panel e) was determined as: (integrated FRET curve)/(integrated emission curve obtained upon direct excitation of YFP at 490 nm). In panels f, g and i, only the FRET emission curves are shown for experiments performed under the indicated conditions. The results shown in each panel are representative of at least 6 independent experiments, with equivalent results.

FIG. 2 shows the oligomerization of α-factor receptors during endocytosis. Fluorescence microscopy was used to localize GFP-tagged tailless receptors co-expressed with untagged wild type receptors (Δtail-GFP+WT) or alone (Δtail-GFP), GFP-tagged glucose transporters expressed with untagged wild type receptors (Hxt1-GFP+WT), and wild type receptors tagged with GFP (WT-GFP). Images were acquired before (0 min) or at the indicated times after the addition of agonist (α-factor, 5 μM). Endosomal vesicles (E), the lysosome-like vacuole (V) and the endoplasmic reticulum (R) are indicated, as documented previously.

FIGS. 3a–3c shows the attenuation of signaling and FRET upon over expression of a dominant-interfering α-factor receptor mutant. Responses of cells to α-factor (growth arrest and gene expression) were used to quantify the signaling efficiencies of cells expressing only wild type receptors or only dominant-interfering mutant receptors (M250I). They were also used to quantify the ability of the dominant-interfering mutant receptor to attenuate signaling when it was overexpressed in cells expressing normal levels of wild type receptors. For assays of agonist-induced reporter gene (FUS1-lacZ) expression (panel a), cells expressed normal levels of either wild type α-factor receptors (WT; closed squares) or the dominant-interfering mutant receptor (M250I; closed circles), or they co-expressed (open squares and open circles) wild type receptors at normal levels and the indicated mutant receptors at elevated levels. For growth arrest assays (panel b), cells expressed normal levels of wild type α-factor receptors and G protein subunits (WT; pictures i–iii), normal levels of wild type α-factor receptors and overexpressed G protein subunits (WT+Gαβγ; pictures iv–vi), or normal levels of a functional α-factor receptor-Gα subunit fusion (WT-Gα; pictures vii–ix). Cells also overexpressed wild type receptors (WT; pictures i, iv, vii), a dominant-interfering mutant receptor (M250I; pictures ii, v, viii), or a dominant-interfering mutant receptor with defective G protein coupling activity (M250I/L236R; pictures iii, vi, ix). Defects in cell responsiveness were quantified by using various doses of agonist (α-factor); response to a single dose of agonist (1.5 nmol) is shown. In panel c, FRET experiments were used to determine the effects of overexpressing an untagged dominant-interfering receptor on interaction between CFP- and YFP-tagged tailless α-factor receptors. Shown are the emission spectra of cells expressing the indicated proteins. The specific FRET emission spectrum was obtained as described in FIG. 1.

DETAILED DESCRIPTION OF THE INVENTION

The present invention may be understood more readily by reference to the following detailed description of the preferred embodiments of the invention and the Example included therein.

Before the present methods are disclosed and described, it is to be understood that this invention is not limited to specific proteins or specific methods. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise.

The present invention provides a method of detecting oligomerization of G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) exciting the fluorescence donor at a particular wavelength; e) detecting fluorescence emission of the acceptor (FRET), such that if this emission is greater than the emission detected in control cells expressing only the acceptor, oligomerization of the G protein coupled receptors has been detected.

In the present invention, "oligomerization" is defined as the association between two or more G protein coupled receptors. Therefore, dimers, trimers, tetramers, pentamers, hexamers, septamers, octamers, nonamers, etc. are all considered oligomers of G protein coupled receptors. Oligomerization can occur between two or more of the same G protein coupled receptors (homologous association) as well as between two or more different G protein coupled receptors (heterologous association). The methods of this invention can be used to detect oligomerization between homologous receptors as well as between heterologous receptors.

The G protein coupled receptors of the present invention include, but are not limited to, α-adrenergic, β-adrenergic, dopaminergic, opioid, opsins, cationic amine, melatonin, purine, chemokine, opioid, glycoprotein hormone receptors, GABA, serotonin, vasopressin, oxytocin, odorant, muscarinic and histamine (see Watson and Arkinstall, "The G Protein Linked Receptor Factsbook" Academic Press, 1994).

The present invention also provides G protein coupled receptor fusion proteins. For the purposes of this invention, a G protein coupled receptor fusion protein is defined as a polypeptide comprising at least a region of a G protein coupled receptor coupled to a fluorescence donor or a fluorescence acceptor. The G protein coupled receptor can be full-length or truncated. For example, the G protein coupled receptors of this invention could be truncated to exclude the C-terminal regulatory region of the GPCR. Alternatively, the G protein coupled receptor could be truncated to include only the first transmembrane domain, the first two transmembrane domains, the first three transmembrane domains, the first four transmembrane domains, the first five transmembrane domains, the first six transmembrane domains or seven transmembrane domains. The invention also contemplates utilizing chimeric G protein coupled receptors, wherein a region of one G protein coupled receptor is linked to another region of a different G protein coupled receptor. For example, one skilled in the art could utilize the methods of this invention to assess oligomerization between a chimeric G protein coupled receptor and a non-chimeric G protein coupled receptor. As an illustrative example, one skilled in the art could obtain a chimeric G protein coupled receptor comprising a region of an α-adrenergic receptor and a region of a β-adrenergic receptor and determine whether or not this chimeric G protein coupled receptor oligomerizes with an α-adrenergic receptor. Alternatively, the skilled artisan could determine whether or not this chimeric G protein coupled receptor oligomerizes with a β-adrenergic receptor. These examples are only illustrative of the numerous possibilities for assessing the interaction between chimeric receptors and non-chimeric receptors.

The G protein coupled receptor fusion proteins of the present invention can be obtained in numerous ways by those skilled in the art. For example, the G protein coupled receptor fusion protein can be purchased from a commercial source. Alternatively, one skilled in the art would know how to make the fusion proteins of the present invention by following the methods in the Example or by making a protein encoded by a nucleic acid where at least a region of a nucleic acid encoding a G protein coupled receptor is coupled to at least a region of a nucleic acid encoding a fluorescence donor or acceptor. Protocols for construction of a vector containing a nucleic acid encoding the fusion protein of this invention are well known in the art (Sambrook et al., *Molecular Cloning: A Laboratory Manual*. 2nd Ed., Cold Spring Harbor Laboratory, Cold Spring Harbor, N.Y. (1989). For example, nucleic acid encoding a G protein coupled receptor or region thereof of this invention can be ligated to a nucleic acid encoding another polypeptide according to standard molecular biology protocols such that a continuous open reading frame results which will allow for production of the fusion protein. The nucleic acid encoding the fusion protein can be placed into an expression vector, which can be obtained commercially or produced in the laboratory. These fusion proteins can be encoded by any nucleic acid that functionally encodes the fusion protein. To functionally encode the protein (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding a selected fusion protein can readily be determined based upon the genetic code for the amino acid sequence of the selected chimeric polypeptide and many nucleic acids will encode any selected chimeric polypeptide. Modifications in the nucleic acid sequence encoding the fusion protein are also contemplated. Modifications that can be useful are modifications to the sequences controlling expression of the fusion protein to make production of the fusion protein inducible or repressible as controlled by the appropriate inducer or repressor. Such means are standard in the art. The nucleic acids can be generated by means standard in the art, such as by recombinant nucleic acid techniques and by synthetic nucleic acid synthesis or in vitro enzymatic synthesis. Alternatively, the G protein coupled receptor fusion proteins of the present invention can be made by chemically conjugating a region of a G protein coupled receptor with a fluorescence donor or acceptor.

The fluorescence donors of the present invention can be any protein or molecule that can be excited at a particular wavelength to transfer energy to a fluorescence acceptor. The fluorescence acceptors of the present invention can be any protein or molecule that can emit energy upon transfer of energy from a fluorescent donor. One skilled in the art would know how to select the appropriate combination of fluorescence donor and fluorescence acceptor to obtain Fluorescence Resonance Energy Transfer (FRET). For example, the donor can be cyan fluorescent protein and the acceptor can be yellow fluorescent protein. In another example, the donor can be blue fluorescent protein and the acceptor can be green fluorescent protein. Red fluorescent protein can also be used as an acceptor with an appropriate donor. One skilled in the art could engineer or identify other bioluminescent donors and acceptors that could be paired to obtain FRET. The skilled artisan would also know how to select the wavelength that excites the fluorescent donor of choice. In addition to the guidance provided in the Example for measurement of FRET, FRET measurements are standard in the art as described in Miyawaki, et al., *Nature* 388, 882–7 (1997). This reference is hereby incorporated by reference to describe the measurement of FRET.

A method of determining whether a receptor agonist activates G protein coupled receptors by enhancing oligomerization or activates G protein coupled receptors by disrupting oligomerization comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; c)exciting the fluorescence donor at a particular wavelength; f) detecting fluorescence resonance energy transfer (FRET), such that if the efficiency of FRET detected is greater in the cells contacted with the agonist than the efficiency of FRET detected in cells prior to the addition of the agonist, receptor activation has occurred by enhancing oligomerization and if the efficiency of FRET detected is less in the cells contacted with the agonist than the efficiency of FRET detected in cells prior to the addition of the agonist, receptor activation has occurred by disrupting oligomerization.

The present invention further provides a method of screening for an agonist that activates G protein coupled receptors by enhancing oligomerization comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; e) exciting the fluorescence donor at a particular wavelength; f) detecting fluorescence resonance energy transfer (FRET), such that if the efficiency of FRET detected is greater in the cells contacted with the agonist than the efficiency of FRET detected in cells prior to the addition of the agonist, receptor activation has occurred by enhancing oligomerization.

Further provided by the present invention is a method of screening for an agonist that activates G protein coupled receptors by disrupting oligomerization comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an agonist; e) exciting the fluorescence donor at a particular wavelength; f) detecting fluorescence resonance energy transfer (FRET), such that if the efficiency of FRET detected is less in the cells contacted with the agonist than the efficiency of FRET detected in cells prior to the addition of the agonist, receptor activation has occurred by disrupting oligomerization.

The present invention also provides a method of screening for an agonist of the interaction between G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); c) contacting the cell with a test compound; d) exciting the fluorescence donor at a particular wavelength; e) detecting fluorescence resonance energy transfer (FRT), such that if the efficiency of FRET detected is greater in cells contacted with the compound than the efficiency of FRET detected in cells prior to the addition of the test compound, the test compound is an agonist of the interaction between G protein coupled receptors.

The agonist of the present invention can be a small molecule, a chemical, a peptide, a region of the natural ligand for the GPCR, a region of a GPCR or any other compound or substance that mimics a ligand for the GPCR, that is able to interact with the receptor, and thereby produces the same action that the natural ligand usually produces. The agonist of the present invention can also be a partial agonist that exhibits levels of activity that are less than that of the natural ligand for the receptor. For example, utilizing the methods of this invention, one skilled in the art could screen test compounds such as small molecules, peptides, chemicals etc. for increased efficiency of FRET. Upon identifying a test compound as an agonist, this agonist can then be administered to subjects with a variety of diseases and disorders when the original ligand that normally interacts with a GPCR is missing, depleted or defective. For example, one could administer a thyrotropin receptor agonist to treat hyperthyroidism, a V2 vasopressin receptor agonist to treat X-linked nephrogenic diabetes insipidus; a beta-adrenergic receptor agonist to treat premature labor, a prostaglandin receptor agonist to induce labor, a serotonin receptor agonist to treat depression, a dopamine receptor agonist to treat Parkinson's disease, a rhodopsin agonist to treat retinitis pigmentosa, or a beta-adrenergic receptor agonist to treat heart failure.

The agonists identified by the methods of the present invention can be screened for selectivity in activating GPCRs. For example, an agonist may activate homologous oligomers of GPCRs as well as heterologous oligomers of GPCRs. However, by utilizing the methods of the present invention, the skilled artisan can compare the differences in FRET for a number of receptors in order to characterize the selectivity of particular agonist. For example, if an agonist activates one GPCR resulting in a 10% increase in FRET efficiency and this agonist also activates a second GPCR resulting in a 25% increase in FRET efficiency, one skilled in the art would know that the agonist preferentially activates the second GPCR The agonists identified by the methods of the present invention can also be assayed for agonist activity in other biological assays. For example, an agonist identified by the methods of the present invention can be assayed for signaling to determine whether or not the agonist identified in the assay exhibits biological properties similar to those of the receptor's natural ligand. Therefore, the methods of this invention can be combined with other biological assays to assess agonist activity.

The present invention also provides a method of screening for an antagonist of the interaction between G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with a test compound; e) exciting the fluorescence donor at a particular wavelength; e) detecting fluorescence resonance energy transfer (FRET), such that if the efficiency of FRET detected is less than the efficiency of FRET detected in cells prior to the addition of the test compound, the test compound is an antagonist of the interaction between G protein coupled receptors.

The antagonist of the present invention can be a small molecule, a chemical, a peptide, a region of the natural ligand for a GPCR, a region of a GPCR or any other compound or substance that interacts with the receptor, and thereby produces the opposite effect that the natural ligand usually produces. The antagonist of this invention can be a partial antagonist and can effect inhibition of the activity of a GPCR ranging from a decrease in activity to complete inhibition of receptor activity. For example, utilizing the methods of this invention, one skilled in the art could screen test compounds which can be small molecules, peptides, chemicals etc. for decreased efficiency of FRET. Upon identifying a test compound as an antagonist, this antagonist can then be administered to subjects with a variety of diseases and disorders where the actions of a particular GPCR need to be inhibited. For example, if there is an excess of the GPCRs natural ligand that is effecting a disease state, an antagonist identified by the methods of this invention can be administered to block the effects of the GPCRs natural ligand. For example, one skilled in the art could administer a leptin receptor antagonist to treat obesity, a dopamine receptor antagonist to treat schizophrenia, a metabotropic glutamate receptor antagonist to treat stroke, a prostaglandin receptor antagonist to treat glaucoma, a TSH receptor antagonist to treat thyroid tumors, a beta-adrenergic receptor antagonist to treat adrenal gland tumors, a lysophosphatidic acid receptor antagonist to treat ovarian cancer, a mu opioid receptor antagonist to treat heroin addiction, a dopamine receptor antagonist to treat cocaine addiction, a mu opioid or prostaglandin receptor antagonist to treat pain, a substance P receptor to treat chronic pain, a histamine receptor antagonist to treat inflammation, a CCR4 chemokine receptor antagonist to treat AIDS, an angiotensin f receptor antagonist to treat hypertension, an angiotensin receptor or endothelin receptor antagonist to treat atherosclerosis, or a fungal receptor antagonist to treat candidiasis. The antagonists of the present invention can act by disrupting oligomerization of GPCRs, or by interacting with the receptor is such a way as to prevent binding of its natural ligand without affecting oligomerization.

The antagonists identified by the methods of the present invention can also be assayed for antagonist activity in other biological assays. For example, an antagonist identified by the methods of the present invention can be assayed for signaling to determine whether or not the antagonist identified in the assay decreases signaling from the receptor. Therefore, the methods of this invention can be combined with other biological assays to assess antagonist activity.

Antagonists that do not affect oligomerization of GPCRs can also be identified by the methods of the present invention. If one skilled in the art has determined that a particular compound is an antagonist, for example, by obtaining dose dependent receptor binding accompanied by decreased signaling for a given receptor, the methods of the present invention can be utilized to determine if the antagonist disrupts oligomerization or antagonizes the GPCR by binding to the GPCR without affecting oligomerization. If the antagonist does not affect FRET, the antagonist does not affect oligomerization of the receptor. Therefore, the present invention also provides a method of determining if an antagonist disrupts oligomerization between G protein coupled receptors comprising: a) obtaining a first G protein coupled receptor fusion protein containing a fluorescence donor; b) obtaining a second G protein coupled receptor fusion protein containing a fluorescence acceptor; c) transfecting a cell with the G protein coupled receptor fusion proteins of a) and b); d) contacting the cell with an antagonist; e) exciting the fluorescence donor at a particular wavelength; f) detecting fluorescence resonance energy transfer (FRET), such that if the efficiency of FRET detected is less than the efficiency of FRET detected in cells prior to the addition of the test compound, the antagonist disrupts oligomerization between G protein coupled receptors and if the efficiency of FRET is unchanged, the antagonist does not disrupt oligomerization between G protein coupled receptors.

The present invention also provides a method of screening for an antagonist of the interaction between constitutively activated G protein coupled receptors comprising: a) obtaining a first constitutively activated G protein coupled receptor fusion protein containing a fluorescence donor; b) obtaining a second constitutively activated G protein coupled receptor fusion protein containing a fluorescence acceptor; c) transfecting a cell with the G protein coupled receptor fusion proteins of a) and b); d) contacting the cell with a test compound; e) exciting the fluorescence donor at a particular wavelength; f) detecting fluorescence resonance energy transfer (FRET), such that if the efficiency of FRET detected is less than the efficiency of FRET detected in cells prior to the addition of the test compound, the test compound is an antagonist of the interaction between constitutively activated G protein coupled receptors. This method can also be performed with one constitutively activated and a second non-constitutively activated receptor that oligomerize and exhibit constitutive activation. Constitutive activation is defined as receptor activation of the receptor in the absence of ligand. As described above, a known antagonist of a particular receptor can also be screened for its ability to antagonize a constitutively activated receptor without disrupting oligomerization.

For example, there are mutant luteinizing hormone receptors that are constitutively activated and result in precocious puberty. Utilizing the methods of this invention, one skilled in the art could screen for compounds that disrupt oligomerization of this constitutively activated receptor. Upon identification of an antagonist, this antagonist can be administered to a subject in order to treat precocious puberty.

The invention also contemplates a method for identifying constitutively activated receptors comprising: a) obtaining a first putative constitutively activated G protein coupled receptor fusion protein containing a fluorescence donor; b) obtaining a second putative constitutively activated G protein coupled receptor fusion protein to containing a fluorescence acceptor; c) transfecting a cell with the G protein coupled receptor fusion proteins of a) and b); d) exciting the fluorescence donor at a particular wavelength; e) detecting the fluorescence resonance energy transfer (FRET); f) comparing the FRET obtained with FRET obtained for the interaction between wildtype G protein coupled receptors in the presence of agonist, such that if the FRET measured for the putative constitutively activated receptors is similar to FRET obtained with the wildtype receptors in the presence of agonist, a constitutively activated G protein coupled receptor has been identified.

The invention also provides methods of detecting the interaction between known or novel components and regulators of signaling pathways that employ G protein coupled receptors. The present invention also contemplates identifying compounds that disrupt these interactions and thereby antagonize or agonize components and regulators of these signaling pathways. These compounds can be used therapeutically to treat diseases associated with G protein coupled receptors. In the following methods, "interaction" or "association" is used to describe the interaction between a G protein coupled receptor and a G protein subunit, or the interaction between G protein subunits, or the interaction between a G protein coupled receptor and a molecule or protein associated with a G protein coupled receptor signaling pathway. For example, the following methods can be adapted to assess the interaction between G protein coupled receptors and other proteins such as G protein coupled receptor kinases, Arrestins, RGS proteins, PDZ domain containing proteins, G protein alpha subunits, G protein beta subunits, G protein gamma subunits, AIDS virus gp120 protein, SH3 domain containing proteins, SH2 domain containing proteins, PTB domain containing proteins and 14-3-3 proteins. The following methods can also be adapted to assess the interaction between G protein subunits, adenylyl cyclases, calcium channels, potassium channels, phosphodiesterase regulatory subunits, phospholipases, G protein coupled receptor kinases, PAK family kinases, RGS proteins, phosducin, AGS proteins, families of MAP kinase cascade proteins, tyrosine kinases, tubulin, actin and proteins involved in G protein-dependent actin assembly.

The present invention further provides a method of detecting the interaction between G protein coupled receptors and G proteins comprising: a) obtaining a G protein subunit containing a fluorescence donor; b) obtaining a G protein coupled receptor fusion protein containing a fluorescence acceptor; c) transfecting a cell with the G protein subunit of a) and the G protein coupled receptor of b); d) exciting the fluorescence donor at a particular wavelength; e) detecting the fluorescence emission of the acceptor (FRET), such that if this emission is greater than the emission detected in control cells expressing only the acceptor, the interaction between the G protein coupled receptor and the G protein subunit has been detected. In the methods of detecting the interaction between G protein coupled receptors and G proteins, the fluorescence donor can be coupled with the G protein coupled receptor or the G protein subunit, and the fluorescence acceptor can be coupled with the G protein coupled receptor or the G protein subunit.

Further provided by this invention is a method of screening for compounds that enhance G protein coupled receptor/G protein interaction comprising: a) obtaining a G protein subunit containing a fluorescence donor; b) obtaining a G protein coupled receptor fusion protein containing a fluorescence acceptor; c) transfecting a cell with the G protein subunit of a) and the G protein coupled receptor of b); d) contacting the well with a test compound; e) exciting the fluorescence donor at a particular wavelength; f) detecting the fluorescence resonance energy transfer (FRET), such that if the efficiency of FRET detected is greater than the efficiency of FRET detected in control cells, the interaction between the G protein coupled receptor and the G protein subunit has been enhanced.

Also provided by this invention is a method of screening for compounds that disrupt G protein coupled receptor/G protein interaction comprising a) obtaining a G protein subunit containing a fluorescence donor; b) obtaining a G protein coupled receptor fusion protein containing a fluorescence acceptor; c) transfecting a cell with the G protein subunit of a) and the G protein coupled receptor of b); d)

contacting the cell with a test compound; e) exciting the fluorescence donor at a particular wavelength; f) detecting the fluorescence resonance energy transfer (FRET), such that if the efficiency of FRET detected is less than the efficiency of FRET detected in control cells, the interaction between the G protein coupled receptor and the G protein subunit has been disrupted.

The invention further provides a method of screening for compounds that are G protein coupled receptor agonists comprising: a) obtaining a G protein subunit containing a fluorescence donor; b) obtaining a G protein coupled receptor fusion protein containing a fluorescence acceptor; c) transfecting a cell with the G protein subunit of a) and the G protein coupled receptor of b); d) contacting the cell with a test compound; e) exciting the fluorescence donor at a particular wavelength; f) detecting the fluorescence resonance energy transfer (FRET), such that if the efficiency of FRET detected is greater than the efficiency of FRET detected in control cells, followed by a decrease in FRET, the compound is a G protein coupled receptor agonist. In this method, the Gα subunit is preferable, however, any other G protein subunit that is involved in the signaling pathway for the G protein coupled receptor can be utilized.

The invention further provides a method of screening for compounds that are G protein coupled receptor antagonists comprising: a) obtaining a G protein subunit containing a fluorescence donor; b) obtaining a G protein coupled receptor fusion protein containing a fluorescence acceptor; c) transfecting a cell with the G protein subunit of a) and the G protein coupled receptor of b); d) contacting the cell with a test compound; e) exciting the fluorescence donor at a particular wavelength; f) detecting the fluorescence resonance energy transfer (FRET), such that if the efficiency of FRET detected is greater than the efficiency of FRET detected in control cells, and is not followed by a decrease in FRET, the compound is a G protein coupled receptor antagonist. In this method, the Go subunit is preferable, however, any other G protein subunit that is involved in the signaling pathway for the G protein coupled receptor can be utilized.

One skilled in the art can also perform time course experiments in order to determine the pattern of increases and decreases of FRET observed for a particular receptor in the presence of agonist or antagonist. For example, upon conducting a time course experiment, if a G protein coupled receptor exhibits an increase in FRET at a particular time followed by a decrease in FRET at another time, in the presence of a known agonist, one would know that other compounds exhibiting a similar patterns of FRET are agonists of the receptor. Similarly, if a G protein coupled receptor exhibits an increase in FRET at a particular time that is not followed by a decrease in FRET at another time (i.e. no reduction or little reduction in the increase in FRET is observed) in the presence of a known antagonist, one would know that other compounds exhibiting a similar patterns of FRET are antagonists of the receptor.

Changes in FRET can also be due to changes in the efficiency of oligomerization and/or changes in the conformations (structures) of the proteins being examined. Such changes in oligomerization and/or conformation are reflective of whether the proteins being studied are switching from an active to an inactive state.

Also provided by the present invention is a method of screening for compounds that disrupt the association between Gα and Gβγ protein subunits comprising: a) obtaining a Gα subunit containing a fluorescence donor; b) obtaining a Gβγ subunit containing a fluorescence acceptor; c) transfecting a cell with the G protein subunits of a) and b); d) contacting the cell with a test compound; e) exciting the fluorescence donor at a particular wavelength; f) detecting the fluorescence resonance energy transfer (FRET), such that if the efficiency of FRET detected is less than the efficiency of FRET detected in control cells, the interaction between the G protein subunits has been disrupted. In the above-described method, Gβγ could be the donor and Gα could be the acceptor.

Also provided by the present invention is a method of screening for compounds that enhance the association between Gα and Gβγ protein subunits comprising: a) obtaining a Gα subunit containing a fluorescence donor; b) obtaining a Gβγ subunit containing a fluorescence acceptor; c) transfecting a cell with the G protein subunits of a) and b); d) contacting the cell with a test compound; e) exciting the fluorescence donor at a particular wavelength; f) detecting the fluorescence resonance energy transfer (FRET), such that if the efficiency of FRET detected is greater than the efficiency of FRET detected in control cells, the interaction between the G protein subunits has been enhanced. In the above-described method, Gβγ could be the donor and Gα could be the acceptor.

The methods of this invention can be performed in intact cells or cell-free preparations of the plasma membrane or recombinant proteins. The G protein subunits of this invention can be obtained from commercially available sources. One skilled in the art would know how to construct a G protein subunit containing a fluorescence donor or acceptor as described above for the construction of the G protein coupled receptor fusion protein. The methods of this invention can be adapted to screen libraries of cDNAs for cDNAs whose expressed product interacts with the G protein subunits or the G protein coupled receptors.

Further provided by the present invention is a G protein coupled receptor fusion protein, comprising a fluorescence donor. Further provided is a G protein coupled receptor fusion protein, comprising a fluorescence acceptor. Also provided are G protein coupled receptor fusion proteins comprising a fluoresence donor or an acceptor that do not contain the C-terminal regulatory domain of the G protein coupled receptor. The fluorescent donors of the G protein coupled receptor fusion proteins can be cyan fluorescent protein. The fluorescent acceptors of the G protein coupled receptor fusion protein can be yellow fluorescent protein.

The invention also provide for a G protein subunit fusion protein comprising a fluoresence donor and a G protein subunit fusion protein comprising a fluoresence acceptor. The G protein subunits of the fusion protein can be full-length or truncated versions of the G protein subunits. The fluorescent donor of the G protein subunit fusion proteins can be cyan fluorescent protein. The fluorescent acceptors of the G protein subunit fusion protein can be yellow fluorescent protein.

As described above, one skilled in the art could obtain the G protein coupled receptor fusion proteins and G protein subunit fusion proteins of the present invention by purchasing them from commercial sources or by making them. The skilled artisan would know how to make the fusion proteins of the present invention by following the methods in the Example or by making a protein encoded by a nucleic acid where at least a region of a nucleic acid encoding a G protein coupled receptor or a G protein subunit is coupled to at least a region of a nucleic acid encoding a fluorescence donor or acceptor. Alternatively, the G protein coupled receptor or the G protein subunit can be chemically conjugated to a fluorescent donor or acceptor.

The following example is intended to illustrate, but not limit, the invention. While the protocols described are typical of those that might be used, other procedures known to those skilled in the art may be alternatively employed.

EXAMPLE

To determine whether GPCRs function as oligomers in vivo, the α-factor receptor (Ste2) of the yeast *S. cerevisiae* was studied. This receptor was used because it was previously shown that it forms SDS-resistant dimers, and it is possible to determine whether oligomerization occurs in a homologous cell type when receptors are expressed at normal levels. Studies of this receptor should be generally applicable because signaling, desensitization and downregulation of α-factor receptors and mammalian GPCRs occur by similar mechanisms (5).

CFP and YFP were joined 8 amino acids (position 304) beyond transmembrane domain VII of the α-factor receptor (STE2 gene product) and at the immediate C-terminus of a glucose transporter (HXT1 gene product). These fusion proteins were expressed from the STE2 promoter on single copy plasmids with different selectable markers, allowing them to be co-expressed at similar levels as shown by quantitation of CFP and YFP fluorescence. Ste2Δtail-CFP and -YFP fusions had normal agonist binding affinities (1–2 nM) and cell surface expression (6–8,000 receptors/cell), as determined by radioligand binding assays. The untagged STE2 and HXT1 genes were overexpressed, respectively, from the constitutive PGK and ADH promoters on high copy plasmids. Yeast cells (KBY58, a ste2Δ mutant) expressing CFP and/or YFP fusion proteins were grown at 30° C. in selective media to a density of $10^7$ cells/ml, washed, suspended in 50 mM PIPES, pH 6.0 and analyzed by scanning fluorometry. Purified plasma membrane fractions were prepared from cells expressing YFP- and/or CFP-tagged tailless receptors, suspended in 100 mM Tris-acetate, pH 8.0, 500 mM K-acetate, 1 mM Mg-acetate, 0.1 mM EDTA, conditions under which agonist binding affinity is sensitive to GTP-γS (K. J. Blumer, J. Thorner, *Proc. Natl. Acad. Sci. USA* 87, 4363–7 (1990)). FRET experiments using plasma membrane fractions employed the same buffer with or without the addition of agonist (5 μM) and/or GTP-γS (50 μM). Cells ($10^7$ cells in 3 ml) or membranes (20 μg protein in 3 ml) were irradiated at 440 nm to excite CFP and fluorescence emission was recorded from 460–610 nm. Data were collected prior to or at various times (1–20 min) after addition of various doses (1 nM-5 μM) of agonist (α-factor) or antagonist (desTrp$_1$,Ala$_3$,Nle$_{12}$-α-factor). FRET was determined by subtracting the emission spectra obtained by excitation (440 nm) of two types of control cells or membrane fractions (one expressing only the CFP-tagged protein and the other expressing only the YFP-tagged protein) from the emission spectrum obtained by excitation (440 nm) of cells or membranes co-expressing equivalent levels of CFP- and YFP-tagged proteins. The efficiency of FRET was big calculated by dividing the integrated FRET spectrum by the integrated emission spectrum obtained upon direct excitation of YFP (490 nm). Among various transformants or membrane preparations, FRET efficiency varied (s.e.m.= 10%) because expression levels of tagged proteins differed up to two-fold. However, when a given transformant or membrane preparation was analyzed the efficiency of FRET was reproducible (s.e.m.=1–2%), and there was no effect of agonist, antagonist or GTP-γS.

A plasmid overexpressing the STE2 coding region from the PGK promoter was mutagenized with hydroxylamine and introduced into wild type cells. Cells expressing dominant-interfering receptors were isolated by plating on selective media containing a concentration of α-factor (50 μM) that arrests growth of the parental strain. Plasmid-dependent α-factor-resistant transformants were identified.

A plasmid that conferred the strongest dominant-interfering phenotype harbored a substitution (M250I) affecting transmembrane domain VI. The M250I mutant receptor exhibited reduced agonist binding affinity (5-fold) but normal cell surface expression, indicating a defect in function rather than expression. A ste2Δ mutant (KBY58) expressing wild type and/or mutant receptors from various plasmids was used for quantitative assays of pheromone response. Methods used to quantify the ability of cells to respond to α-factor (growth arrest and agonist induction of the FUS1-lacZ reporter) have been described (7); standard errors were less than 10% of the mean. Oligonucleotide-directed mutagenesis was used to introduce the L236R substitution in cis in the dominant-interfering receptor, producing the M250I/L236R double mutant receptor. The α, β and γ subunits of the G protein involved in α-factor response were overexpressed from a high copy plasmid carrying all three coding regions (GPA1, STE4, STE18) expressed from their normal promoters. An α-factor receptor-Gα subunit fusion was constructed by appending the GPA1 coding region to the last codon of the STE2 gene expressed from its normal promoter on a centromeric plasmid; the resultant fusion was fully functional (R. Medici, E. Bianchi, G. Di Segni, G. P. Tocchini-Valentini, *Embo J* 16, 7241–9 (1997)).

CFP- and YFP-based fluorescence resonance energy transfer (FRET; ref. 6) was utilized to determine whether α-factor receptors form oligomers in vivo. FRET can occur over a distance of up to 100 Å (6), within the center-to-center distance (~40 Å) between subunits of a GPCR oligomer as suggested by the dimensions of a rhodopsin monomer (7). Furthermore, FRET is extraordinarily sensitive to interfluorophore distance, orientation or mobility, providing a means of determining whether agonist binding changes the quaternary structure of a GPCR.

FRET experiments were performed using truncated α-factor receptors lacking their cytoplasmic C-terminal regulatory domains (Ste2Δtail-CFP, donor; Ste2Δtail-YFP, acceptor), which are normal with respect to expression level, agonist binding affinity and G protein activation (8). Truncated receptors were used to reduce interfluorophore distance or mobility, improving the likelihood of detecting FRET, and to eliminate phosphorylation and ubiquitination of the receptor, which are required for desensitization and endocytosis. This ensured that FRET would not detect interactions between desensitized or internalized receptors.

Figure 1A:
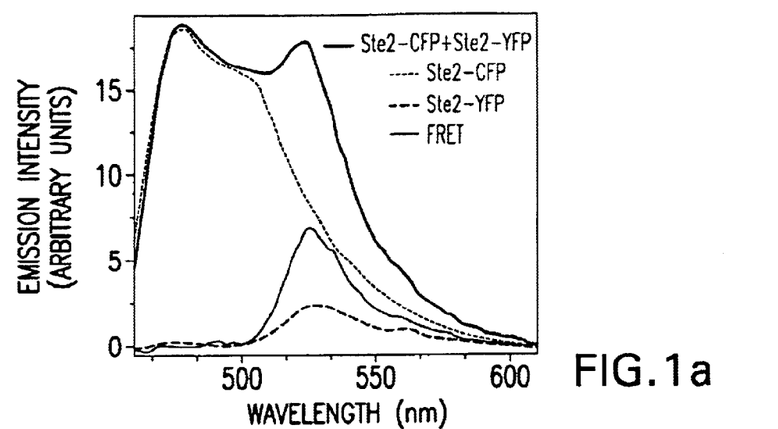

FRET was detected between Ste2Δtail-CFP and Ste2Δtail-YFP co-expressed at wild type levels (FIG. 1*a*). In contrast, FRET was not detected between CFP- and YFP-tagged full-length receptors, indicating a dependence on interfluorophore distance, orientation or mobility.

Figure 1B:
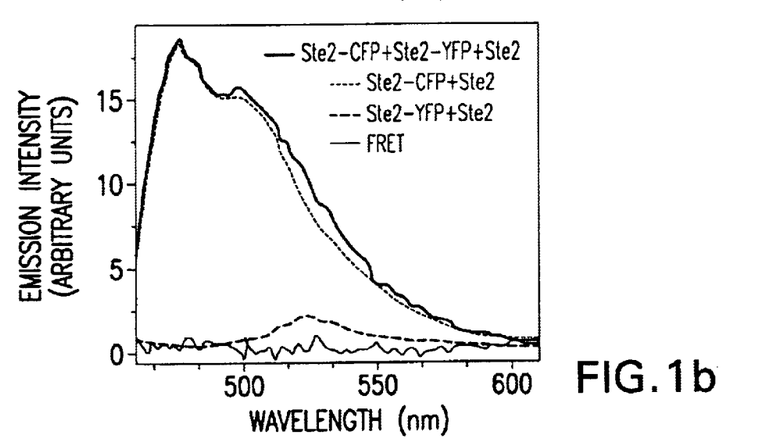
Figure 1C:
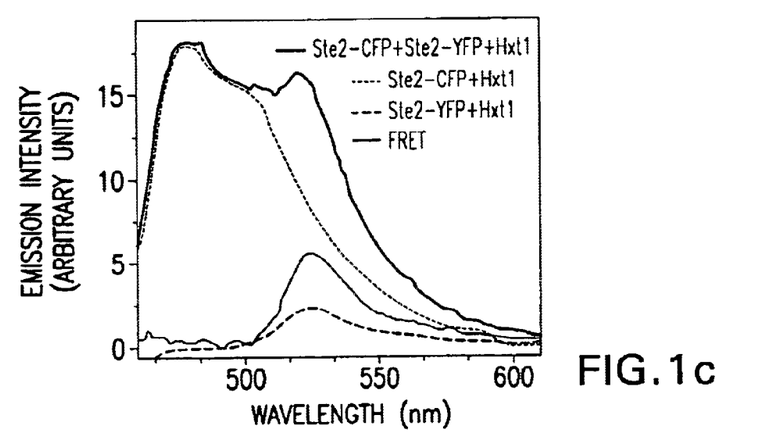
Figure 1D:
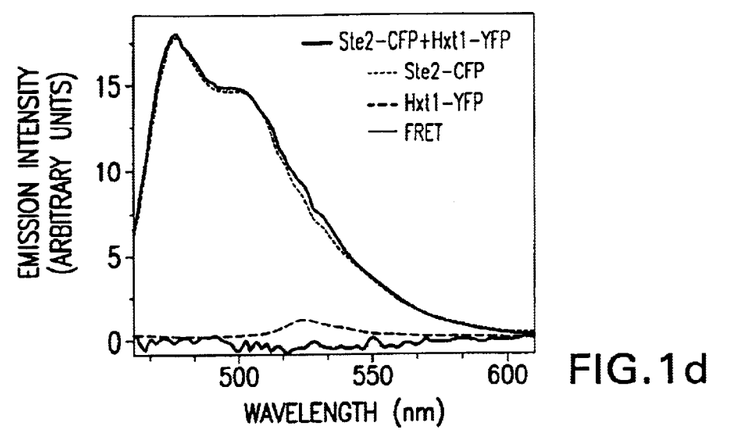
Figure 1E:
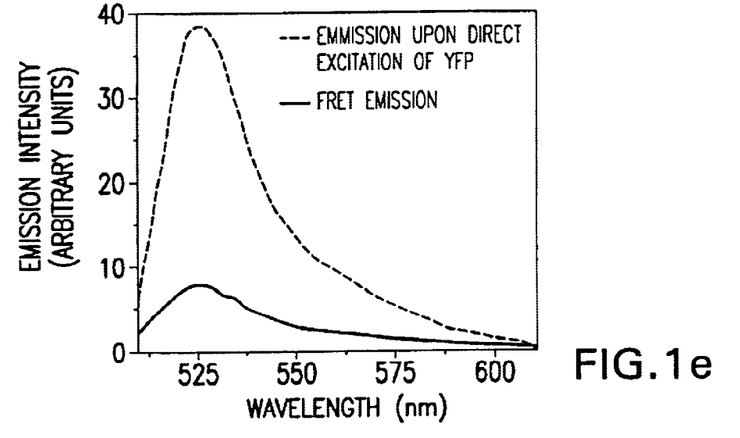
Figure 1F:
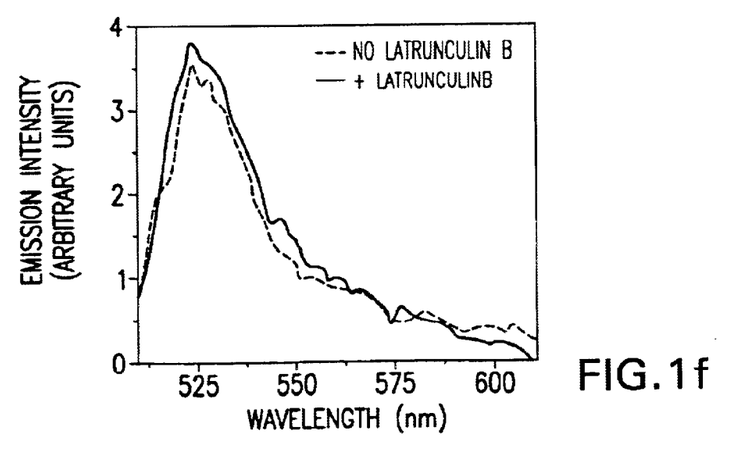

Several results indicated that FRET was due to a direct, specific, homophilic interaction between tailless receptors, and not due to dimerization via CFP and YPF, non-specific collisional interaction, or an indirect interaction mediated by the cortical actin cytoskeleton. First, FRET was not detected when untagged receptors were overexpressed (FIG. 1*b*), even though the tagged receptors were expressed normally at the cell surface as indicated by quantitation of CFP and YFP fluorescence and by fluorescence microscopy. Inhibition of FRET by untagged receptors was specific because over expression of a plasma membrane glucose transporter (Hxt1) at a similar level did not affect FRET between tagged receptors (FIG. 1c). Specific inhibition of FRET by overexpressed wild type receptors also suggested that wild type receptors oligomerize. Second, FRET was not detected between CFP-tagged tailless receptors and YFP-tagged glucose transporters (FIG. 1d), indicating that random collisional interactions between plasma membrane proteins does not cause FRET. Third, a stable, specific interaction between α-factor receptors was indicated by the high apparent efficiency of FRET (18±1%, n=7; FIG. 1e). Fourth, FRET was detected when the actin cytoskeleton was disassembled by treating cells with latrunculin B (FIG. 1f).

Figure 1G:
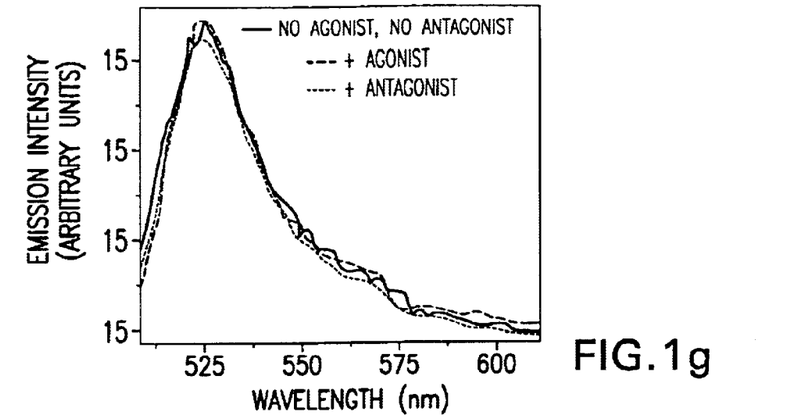

The apparent efficiencies of FRET observed with control cells and cells treated with agonist or antagonist were indistinguishable (18%±1, n=6), as indicated by dose-response and time course experiments using sub-saturating to saturating ligand concentrations (FIG. 1g). Therefore, stabilization of α-factor receptors in either an active or inactive conformation was not accompanied by substantial changes in monomer-oligomer equilibrium. However, agonist or antagonist binding could affect receptor distribution among oligomeric states (e.g.-dimers and tetramers), which would not necessarily affect FRET efficiency.

Figure 1H:
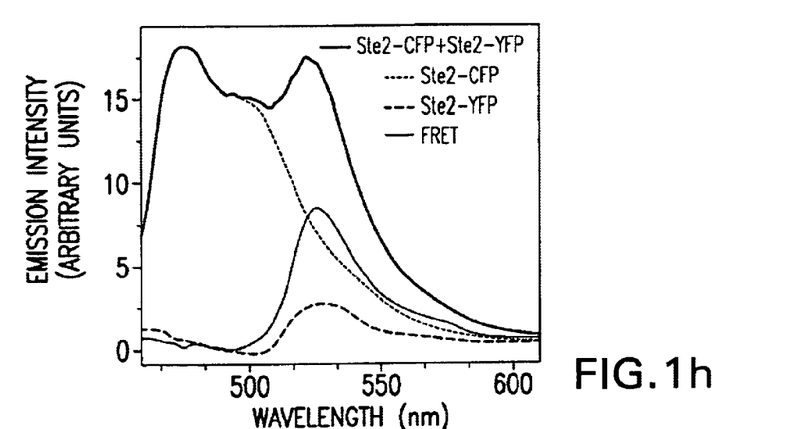
Figure 1I:
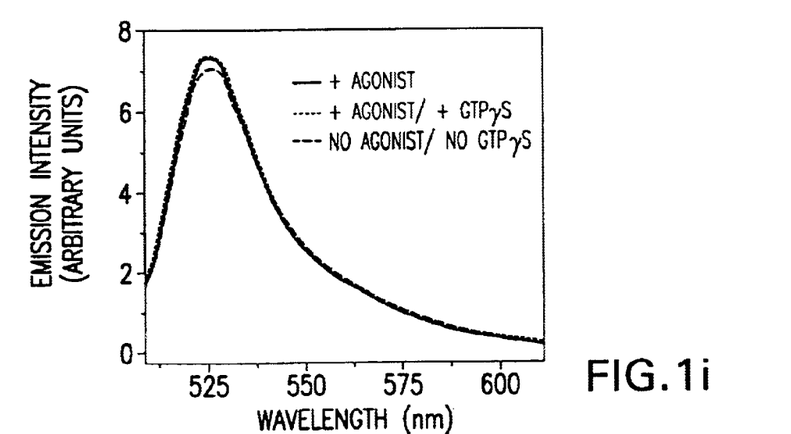

FRET was also observed in experiments using purified plasma membrane fractions derived from cells co-expressing Ste2Δtail-CFP and Ste2Δtail-YFP (FIG. 1h). This result allowed determination of whether or not monomer-oligomer equilibrium is affected by the formation of receptor-G protein ternary complexes, or by the sustained activation and dissociation of G protein subunits from the receptor. It was found that the apparent efficiency of FRET (20%±2%, n=11) in plasma membrane fractions was indistinguishable whether receptors and G proteins were inactive (no agonist or GTP-γS; FIG. 1i), had formed ternary complexes (5 μM agonist without GTP-γS; FIG. 1i), or were activated and uncoupled (5 μM agonist and 50 μM GTP-γS; FIG. 1i). These results reinforced the conclusion that monomer-oligomer equilibrium is unaffected by signaling.

Figure 2:
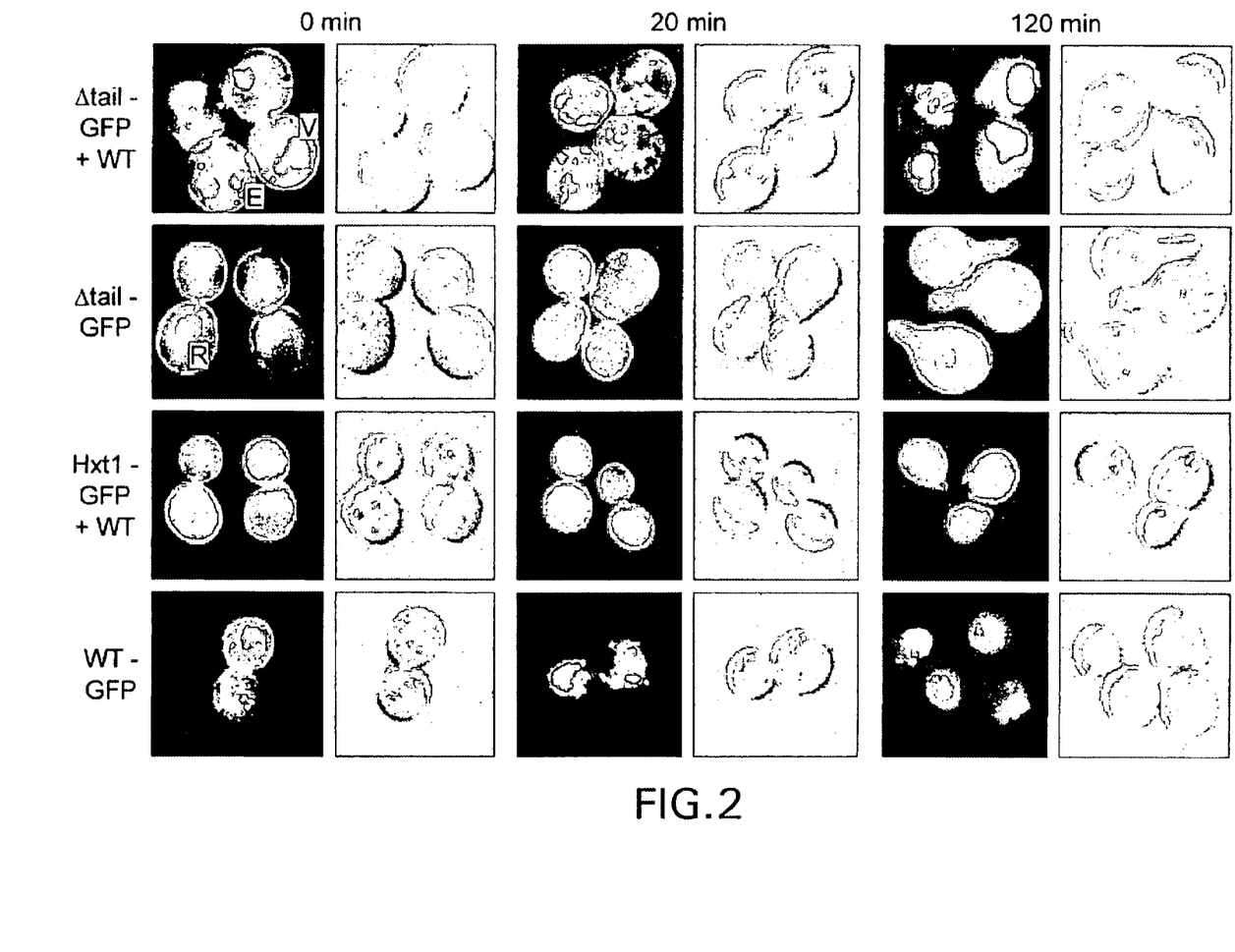

Independent evidence of receptor oligomerization in vivo was obtained by showing that the endocytosis defect of tailless receptors (Δtail-GFP) was corrected upon coexpression of untagged wild type receptors (WT; FIG. 2). Agonist-independent endocytosis of GFP-tagged tailless receptors was indicated by fluorescence labeling of endosomal vesicles and the large lysosome-like vacuole, as occurs when cells express full-length GFP-tagged receptors (FIG. 2). Agonist-induced internalization was indicated by time-dependent decreases in the level of cell surface GFP-tagged tailless receptors and increases in labeling of endosomes and the vacuole. The ability of wild type receptors to rescue the endocytosis defect of tailless receptors was not due to stimulation of bulk internalization of plasma membrane proteins, because a glucose transporter-GFP fusion (Hxt1-GFP) was not internalized when coexpressed with untagged wild type receptors either with or without agonist stimulation (FIG. 2). In contrast, tailless GFP-tagged receptors expressed alone did not undergo basal or agonist induced endocytosis, as indicated by their persistence at the plasma membrane and their inability to localize to endosomes or the vacuole (FIG. 2). Thus, α-factor receptors are oligomeric during basal and agonist-induced internalization, in accord with results of FRET experiments showing that these receptors interact in the absence and presence of agonist.

If oligomerization is required for normal signaling, then cells expressing wild type receptors should signal inefficiently if they also overexpress signaling-defective receptors that interact with wild type receptors. Signal inhibition could occur if mutant receptor subunits interfere with the ability of wild type receptor subunits to undergo agonist induced conformational changes or to activate G protein heterotrimers. Accordingly, dominant-interfering mutant receptors were selected that inhibit signaling when overexpressed in cells expressing normal levels of wild type receptors. This approach identified a novel substitution (M250I) in transmembrane segment VI, a domain that controls activation of the α-factor receptor (9).

Figure 3A:
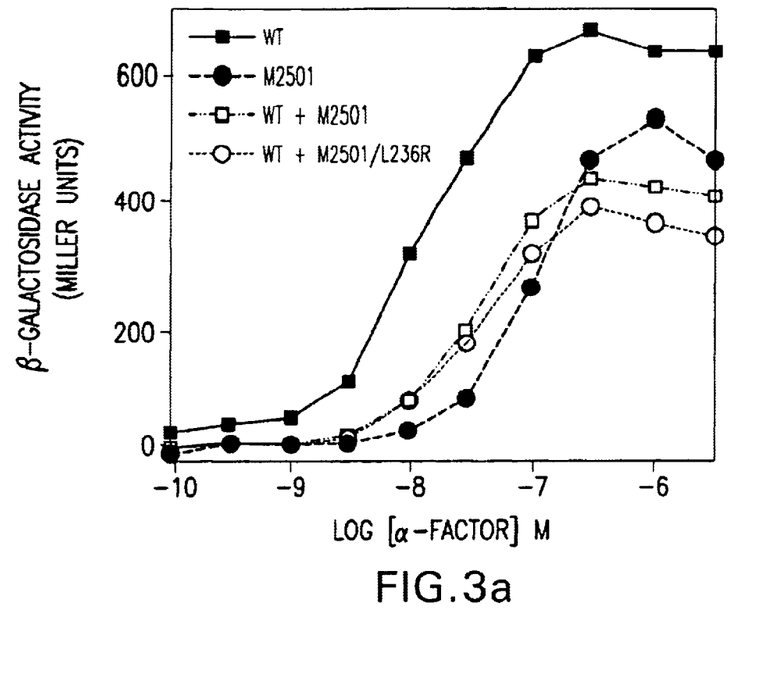
Figure 3B:
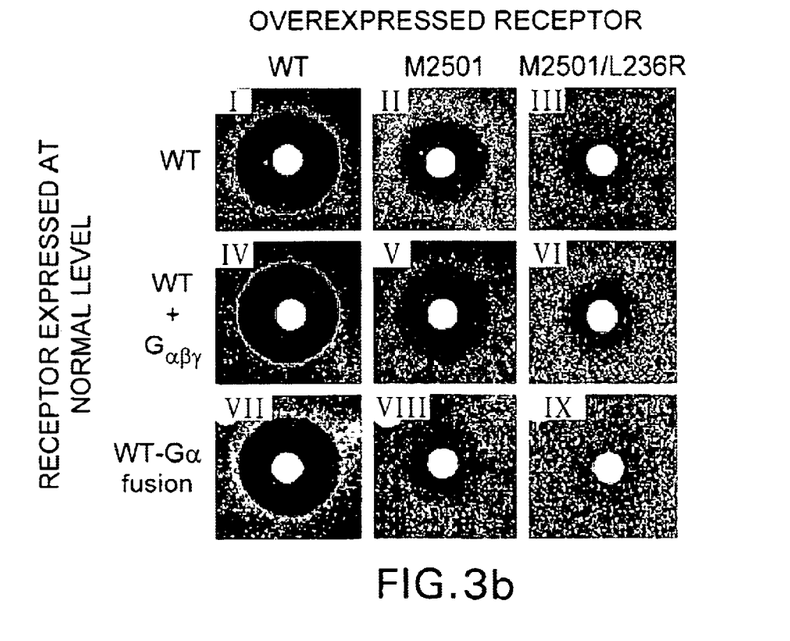
Figure 3C:
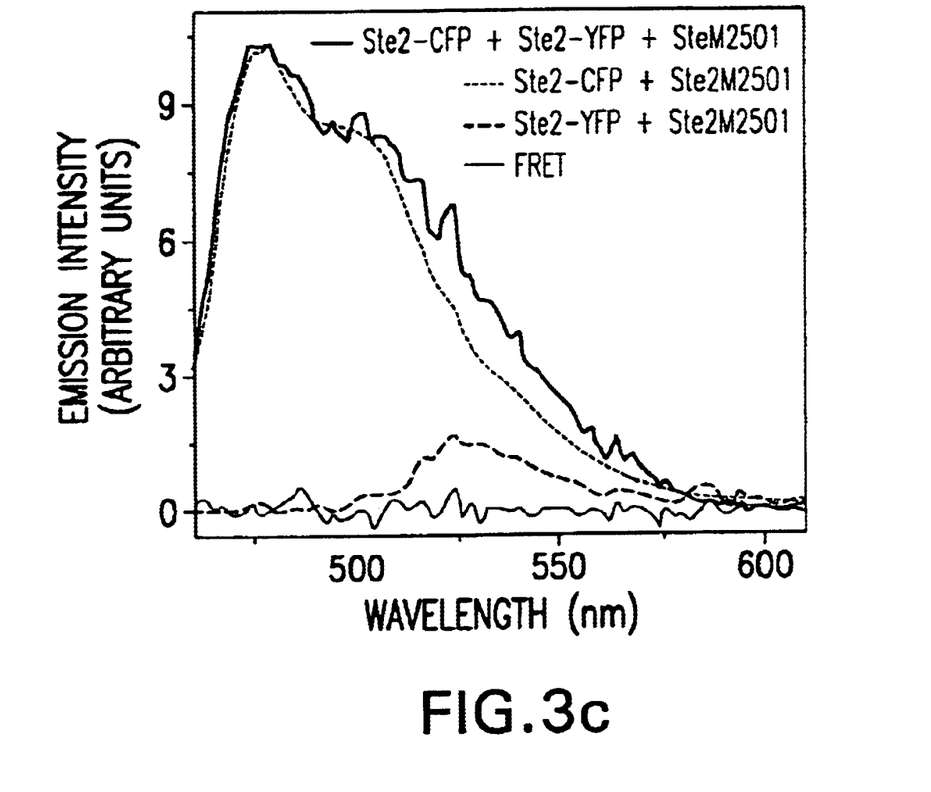

The dominant-interfering receptor could inhibit signaling by interacting with wild type receptors, or by sequestering a limiting pool of G protein heterotrimers. Several results supported the receptor interaction mechanism of inhibition. First, over expression of mutant receptors blocked FRET between CFP- and YFP-tagged tailless receptors without affecting expression of tagged receptors. Second, signaling efficiency (agonist-induced reporter gene expression) was attenuated to a similar extent (3- to 5-fold decrease in agonist potency and a 40% decrease in agonist efficacy) whether cells expressed only the mutant receptor at normal levels, or whether they expressed wild type receptors at normal levels and overexpressed mutant receptors 5- to 10-fold (FIG. 3a,b). This result suggests that herterooligomers containing mutant and wild type receptors have reduced activity that is similar to oligomers consisting only of mutant receptors. Third, a G protein sequestration mechanism was ruled out because a dominant-interfering phenotype (attenuation of agonist-induced growth arrest and/or reporter gene expression) was still observed when: i) the ability of the mutant receptor to interact with G proteins was disrupted (by introducing the L236R substitution (ref 12) in cis in its third cytoplasmic loop; FIG. 3a and 3b, panels iii, vi, ix); ii) G protein α, β and γ subunits were overexpressed (FIG. 3b, panels iv–vi); and iii) the wild type receptor was fused to the Gα subunit (FIG. 3b, panels vii–ix). Therefore, oligomerization of α-factor receptors is required for efficient signal transduction. Fourth, the dominant-interfering receptor retained the ability fo interact with wild type receptors, as indicated by its ability to interfere with FRET between wild type receptors (FIG. 3c).

These results show that GPCRs form oligomers in vivo, that monomer-oligomer equilibrium in vivo is largely unaffected by agonist or G protein binding, and that oligomerization is required for efficient signal transduction.

Oligomerization is likely to be a general mechanism that is required for several aspects of GPCR function and regulation. Efficient receptor-G protein coupling could involve interaction between a receptor dimer and a single G protein heterotrimer. Thus, novel receptor subtypes that are found in native tissues may be generated by heterooligomerization of known GPCR subtypes.

Throughout this application, various publications are referenced. The disclosures of these publications in their entireties are hereby incorporated by reference into this application in order to more fully describe the state of the art to which this invention pertains.

REFERENCES

1. T. E. Hebert, et al., *J Biol Chem* 271, 16384–92 (1996).
2. K. J. Blumer, J. E. Reneke, J. Thorner, *J Boil Chem* 263, 10836–42 (1988); G. Y. Ng, et al., *Biochem Biophys Res Commun* 227, 200–4 (1996); C. Romano, W. L. Yang, K. L. O'Malley, *J Boil Chem* 271, 28612–6 (1996); M. Bai, S. Trivedi, E. M. Brown, *J Biol Chem* 273, 23605–10 (1998); S. Cvejic, L A. Devi, *J Biol Chem* 272, 26959–64 (1997).

3. J. H. White, et al., *Nature* 396, 679–82 (1998); K. A. Jones, et al., *Nature* 396, 674–9 (1998); B. A. Jordan, L. A. Devi, *Nature* 399, 697–700 (1999).
4. T. E. Hebert, M. Bouvier, *Biochem Cell Biol* 76, 1–11 (1998); J. Bockaert, J. P. Pin, *Embo J* 18, 1723–9 (1999); P. R. Gouldson, C. R. Snell, R. P. Bywater, C. Higgs, C. A. Reynolds, *Protein Eng* 11, 1181–93 (1998).
5. L. Bardwell, J. G. Cook, C. J. Inouye, J. Thorner, *Developmental Biology* 166, 363–79 (1994).
6. A. Miyawaki, et al., *Nature* 388, 882–7 (1997).
7. V. M. Unger, P. A. Hargrave, J. M. Baldwin, G. F. Schertler, *Nature* 389, 203–6 (1997).
8. J. E. Reneke, K. J. Blumer, W. E. Courchesne, J. Thomer, *Cell* 55, 221–34 (1988); C. J. Stefan, K. J. Blumer, *J Boil Chem* 274, 1835–41 (1999).
9. C. J. Stefan, M. C. Overton, K. J. Blumer, *Mol Biol Cell* 9, 885–99 (1998).
10. J. L. Weiner, S. C. Guttierez, K. J. Blumer, *J. Biol. Chem.* 268, 8070–7 (1993).
11. R. Maggio, Z. Vogel, J. Wess, *Proc Natl Acad Sci USA* 90, 3103–7 (1993); R. Maggio, P. Barbier, F. Fornai, G. U. Corsini, *J Biol Chem* 271, 31055–60 (1996); C. Monnot, et al., *J Biol Chem* 271, 1507–13 (1996); Y. Osuga, et al., *J Biol Chem* 272, 25006–12 (1997); P. M. Conn, D. C. Rogers, J. M. Stewart, J. Niedel, T. Sheffield, *Nature* 296, 653–5 (1982).
12. G. Schertler, P. A. Hargrave, *Proc. Natl. Acad. Sci. USA* 92, 11578–11582 (1995).
13. R. Onrust, et al., *Science* 275, 381–4 (1997).
14. S. M. Wade, H. M. Dalman, S. Z. Yang, R. R. Neubig, *Mol Pharmacol* 45, 1191–7 (1994).
15. A. L. Nordstrom, L. Farde, L. Eriksson, C. Halldin, *Psychiatry Res* 61, 67–83 (1995).

What is claimed is:

1. A method of detecting oligomerization of G protein coupled receptors comprising:
    a) transfecting a cell with a polynucleotide encoding a first G protein-coupled receptor fusion protein comprising a fluorescence acceptor and a polynucleotide encoding a second G protein-coupled receptor fusion protein comprising a fluorescence donor;
    b) exciting the fluorescence donor at a particular wavelength;
    c) detecting fluorescence emission of the acceptor (FRET), such that if this emission is greater than the emission detected in control cells expressing only the acceptor, oligomerization of the G protein coupled receptors has been detected.

2. The method of claim 1, wherein the first and second G protein coupled receptor regions of the fusion proteins are the same.

3. The method of claim 1, wherein the first and second G protein coupled receptor regions of the fusion proteins are different.

4. The method of claim 1, wherein the fluorescence donor is cyan fluorescent protein and the fluorescence acceptor is yellow fluorescent protein.

5. The method of claim 1, wherein the polynucleotide encoding the first G protein coupled receptor encodes a truncated G protein coupled receptor.

6. A method of determining whether a receptor agonist activates G protein coupled receptors by enhancing oligomerization or activates G protein coupled receptors by disrupting oligomerization comprising:
    a) transfecting a cell with a polynucleotide encoding a first G protein-coupled receptor fusion protein comprising a fluorescence acceptor and a polynucleotide encoding a second G protein-coupled receptor fusion protein comprising a fluorescence donor;
    b) contacting the cell with an agonist;
    c) exciting the fluorescence donor at a particular wavelength;
    d) detecting fluorescence resonance energy transfer (FRET), such that if the efficiency of FRET detected is greater in the cells contacted with the agonist than the efficiency of FRET detected in cells prior to the addition of the agonist, receptor activation has occurred by enhancing oligomerization and if the efficiency of FRET detected is less in the cells contacted with the agonist than the efficiency of FRET detected in cells prior to the addition of the agonist, receptor activation has occurred by disrupting oligomerization.

7. The method of claim 6, wherein the first and second G protein coupled receptor regions of the fusion proteins are the same.

8. The method of claim 6, wherein the first and second G protein coupled receptor regions of the fusion proteins are different.

9. The method of claim 6, wherein the fluorescence donor is cyan fluorescent protein and the fluorescence acceptor is yellow fluorescent protein.

10. The method of claim 6, wherein the polynucleotide encoding the first G protein coupled receptor encodes a truncated G protein coupled receptor.

11. A method of screening for an agonist of the interaction between G protein coupled receptors comprising:
    a) transfecting a cell with a polynucleotide encoding a first G protein-coupled receptor fusion protein comprising a fluorescence acceptor and a polynucleotide encoding a second G protein-coupled receptor fusion protein comprising a fluorescence donor;
    b) contacting the cell with a test compound;
    c) exciting the fluorescence donor at a particular wavelength;
    d) detecting fluorescence resonance energy transfer (FRET), such that if the efficiency of FRET detected is greater in cells contacted with the compound than the efficiency of FRET detected in cells prior to the addition of the test compound, the test compound is an agonist of the interaction between G protein coupled receptors.

12. The method of claim 11, wherein the first and second G protein coupled receptor regions of the fusion proteins are the same.

13. The method of claim 11, wherein the first and second G protein coupled receptor regions of the fusion proteins are different.

14. The method of claim 11, wherein the fluorescence donor is cyan fluorescent protein and the fluorescence acceptor is yellow fluorescent protein.

15. The method of claim 11, wherein the polynucleotide encoding the first G protein coupled receptor encodes a truncated G protein coupled receptor.

16. A method of screening for an antagonist of the interaction between G protein coupled receptors comprising:
    a) transfecting a cell with a polynucleotide encoding a first G protein-coupled receptor fusion protein comprising a fluorescence acceptor and a polynucleotide encoding a second G protein-coupled receptor fusion protein comprising a fluorescence donor;
    b) contacting the cell with a test compound;
    c) exciting the fluorescence donor at a particular wavelength;
    d) detecting fluorescence resonance energy transfer (FRET), such that if the efficiency of FRET detected is less than the efficiency of FRET detected in cells prior to the addition of the test compound, the test compound is an antagonist of the interaction between G protein coupled receptors.

17. The method of claim 16, wherein the first and second G protein coupled receptor regions of the fusion proteins are the same.

18. The method of claim 16, wherein the first and second G protein coupled receptor regions of the fusion proteins are different.

19. The method of claim 16, wherein the fluorescence donor is cyan fluorescent protein and the fluorescence acceptor is yellow fluorescent protein.

20. The method of claim 16, wherein the polynucleotide encoding the first G protein coupled receptor encodes a truncated G protein coupled receptor.

21. The method of claim 1, wherein the polynucleotide encoding the second G protein coupled receptor encodes a truncated G protein coupled receptor.

22. The method of claim 6, wherein the polynucleotide encoding the second G protein coupled receptor encodes a truncated G protein coupled receptor.

23. The method of claim 11, wherein the polynucleotide encoding the second G protein coupled receptor encodes a truncated G protein coupled receptor.

24. The method of claim 16, wherein the polynucleotide encoding the second G protein coupled receptor encodes a truncated G protein coupled receptor.

* * * * *